US012735677B2

(12) United States Patent
Ishikawa et al.

(10) Patent No.: US 12,735,677 B2
(45) Date of Patent: Sep. 15, 2026

(54) METHOD FOR PRODUCING ASTROCYTE-LIKE CELLS

(71) Applicants: JSR CORPORATION, Tokyo (JP); KEIO UNIVERSITY, Tokyo (JP)

(72) Inventors: Mitsuru Ishikawa, Tokyo (JP); Hideyuki Okano, Tokyo (JP)

(73) Assignees: JSR CORPORATION, Tokyo (JP); KEIO UNIVERSITY, Tokyo (JP)

( * ) Notice: Subject to any disclaimer, the term of this patent is extended or adjusted under 35 U.S.C. 154(b) by 728 days.

(21) Appl. No.: 18/116,349

(22) Filed: Mar. 2, 2023

(65) Prior Publication Data

US 2023/0203438 A1 Jun. 29, 2023

Related U.S. Application Data

(63) Continuation of application No. PCT/JP2021/033103, filed on Sep. 9, 2021.

(30) Foreign Application Priority Data

Sep. 10, 2020 (JP) ................................ 2020-152180

(51) Int. Cl.
*C12N 5/079* (2010.01)

(52) U.S. Cl.
CPC ........ *C12N 5/0622* (2013.01); *C12N 2501/10* (2013.01); *C12N 2501/60* (2013.01); *C12N 2506/45* (2013.01)

(58) Field of Classification Search
None
See application file for complete search history.

(56) References Cited

U.S. PATENT DOCUMENTS

2022/0333070 A1* 10/2022 Ahlenius .............. C12N 15/635

FOREIGN PATENT DOCUMENTS

WO WO-2017057523 A1 4/2017
WO WO-2018175574 A1 9/2018

OTHER PUBLICATIONS

Sofroniew MV, Vinters HV. Astrocytes: biology and pathology. Acta Neuropathol. Jan. 2010;119(1):7-35. doi: 10.1007/s00401-009-0619-8. Epub Dec. 10, 2009. PMID: 20012068; PMCID: PMC2799634. (Year: 2010).*

Li S, Zhang A, Xue H, Li D, Liu Y. One-Step piggyBac Transposon-Based CRISPR/Cas9 Activation of Multiple Genes. Mol Ther Nucleic Acids. Sep. 15, 2017;8:64-76. doi: 10.1016/j.omtn.2017.06.007. Epub Jun. 15, 2017. PMID: 28918057; PMCID: PMC5485764. (Year: 2017).*

Woodard LE, Wilson MH. piggyBac-ing models and new therapeutic strategies. Trends Biotechnol. Sep. 2015;33(9):525-33. doi: 10.1016/j.tibtech.2015.06.009. Epub Jul. 23, 2015. PMID: 26211958; PMCID: PMC4663986. (Year: 2015).*

Canals I., et al., "Rapid and efficient induction of functional astrocytes from human pluripotent stem cells", Nature Methods., vol. 15, pp. 693-696 (plus cover pages), 2018.

International Search Report issued Nov. 30, 2021 in PCT/JP2021/033103 (with English translation), 6 pages.

Li X., et al., "Fast Generation of Functional Subtype Astrocytes from Human Pluripotent Stem Cells", Stem Cell Reports, vol. 11, pp. 998-1008, 2018.

Extended European Search Report issued Oct. 28, 2024, in corresponding European Patent Application No. 21866815.0, 10 pages.

Massimiliano Caiazzo, et al., "Direct Conversion of Fibroblasts into Functional Astrocytes by Defined Transcription Factors", Stem Cell Reports, vol. 4, No. 1, Jan. 2015, pp. 25-36, XP055376127.

* cited by examiner

*Primary Examiner* — Christopher M Babic
*Assistant Examiner* — Alyssa G Weston
(74) *Attorney, Agent, or Firm* — Element IP, PLC

(57) ABSTRACT

A method is provided for producing astrocyte-like cells, including (A) upregulating transcription factors including SRY-box transcription factor 9 (SOX9), nuclear factor IA (NFIA), and nuclear factor IB (NFIB) in human pluripotent stein cells and (B) culturing the human pluripotent stem cells, in which the transcription factors are upregulated, and consequently differentiating the human pluripotent stem cells into astrocyte-like cells.

8 Claims, 5 Drawing Sheets

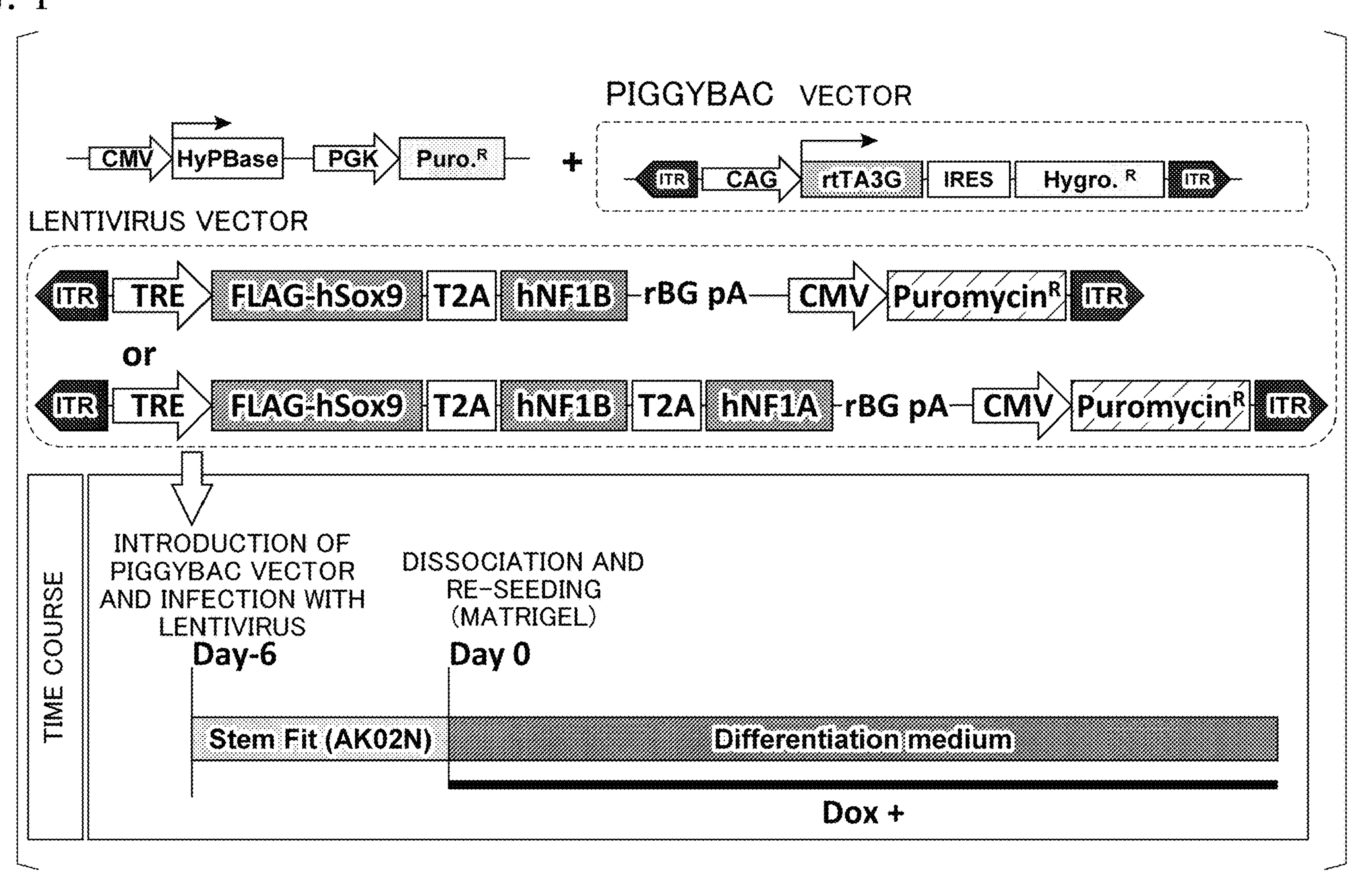
FIG. 1
PIGGYBAC VECTOR
CMV
HyPBase
PGK
Puro.R
+
ITR
CAG
rtTA3G
IRES
Hygro. R
ITR
LENTIVIRUS VECTOR
ITR
TRE
FLAG-hSox9
T2A
hNF1B
rBG pA
CMV
PuromycinR
ITR
or
ITR
TRE
FLAG-hSox9
T2A
hNF1B
T2A
hNF1A
rBG pA
CMV
PuromycinR
ITR
TIME COURSE
INTRODUCTION OF PIGGYBAC VECTOR AND INFECTION WITH LENTIVIRUS
Day-6
DISSOCIATION AND RE-SEEDING (MATRIGEL)
Day 0
Stem Fit (AK02N)
Differentiation medium
Dox +

GFAP

S100β mRNA EXPRESSION
(fold-increase)

5
4
3
2
1
0

10
8
6
4
2
0

(−) NF1A (−) NF1A

SOX9 + NF1B

SOX9 + NF1B

METHOD FOR PRODUCING ASTROCYTE-LIKE CELLS

BACKGROUND OF THE INVENTION

Field of the Invention

The present invention relates to a method for producing astrocyte-like cells. More specifically, the present invention relates to a method for producing astrocyte-like cells, astrocyte-like cells, a co-culture of astrocyte-like cells and nerve-like cells, and use of a culture medium for producing astrocyte-like cells. Priority is claimed on Japanese Patent Application No. 2020-152180, filed Sep. 10, 2020, the content of which is incorporated herein by reference.

Description of Related Art

There is a demand for using nervous system tissues for basic research, elucidation of nervous system diseases, and the like. However, experimental results obtained using nervous system tissues of experimental animals such as mice and rats may have problems in terms of extrapolation to humans, and there are limitations on the use of human nervous system tissues. For this reason, the in vitro formation and use of human nervous system tissues have been examined.

However, it is known that brain organoids produced from pluripotent stein cells such as induced pluripotent stem (iPS) cells are mainly composed of nerve cells and neural stem cells and do not include fully mature glial cells (astrocytes, oligodendrocytes, microglia, and the like).

It has been revealed that glial cells are responsible for the survival and exhibition of functions of nerve cells, such as the supply of nutrients to nerve cells, and not only nerve cells but also glial cells play an important role in the exhibition of brain function. As a result, there is a need for techniques to generate glial cells in vitro.

For example, Non-Patent Document 1 describes that human pluripotent stem cells have been induced to differentiate into astrocyte-like cells by overexpressing an SRY-box transcription factor 9 (SOX9) gene and a nuclear factor IB (NFIB) gene.

In addition, Non-Patent Document 2 describes that human pluripotent stem cells have been induced to differentiate into astrocyte-like cells by overexpressing a nuclear factor IA (NFIA) gene, or a SOX9 gene and an NFIA gene.

CITATION LIST

Non-Patent Documents

Non-Patent Document 1

Canals I., et al., Rapid and efficient induction of functional astrocytes from human pluripotent stein cells, Nat Methods, 693-696, 2018.

Non-Patent Document 2

Li X., et al., Fast Generation of Functional Subtype Astrocytes from Human Pluripotent Stem Cells, Stem Cell Reports, 998-1008, 2018.

SUMMARY OF INVENTION

Technical Problem

An object of the present invention is to provide a technique for efficiently producing astrocyte-like cells in vitro.

Solution to Problem

The present invention includes the following aspects.

[1] A method for producing astrocyte-like cells, including:

a step (A) of upregulating transcription factors including SRY-box transcription factor 9 (SOX9), nuclear factor IA (NFIA), and nuclear factor IB (NFIB) in human pluripotent stem cells; and a step (B) of culturing the human pluripotent stem cells, in which the transcription factors are upregulated, and consequently differentiating the human pluripotent stem cells into astrocyte-like cells.

[2] The method for producing astrocyte-like cells according to [1], in which in the step (B), the human pluripotent stem cells are cultured in a culture medium for pluripotent stem cell culturing or a culture medium for nerve cell culturing.

[3] The method for producing astrocyte-like cells according to [1] or [2], in which the step (A) is carried out by introducing vectors containing nucleic acids encoding the transcription factors into the human pluripotent stem cells.

[4] The method for producing astrocyte-like cells according to [1] or [2], in which the step (A) is carried out by adding or removing a tetracycline-based antibiotic to or from a culture medium of the human pluripotent stem cells into which vectors containing nucleic acids encoding the transcription factors under regulation of a tetracycline response element are introduced.

[5] The method for producing astrocyte-like cells according to [3] or [4], in which the vector contains a nucleic acid consisting of a base sequence represented by Formula (1), $$F^1\text{-}S^1\text{-}F^2\text{-}S^2\text{-}F^3 \quad (1)$$

[in Formula (1), $F^1$, $F^2$, and $F^3$ represent, in no particular order, a base sequence encoding SOX9, a base sequence encoding NFIA, and a base sequence encoding NFIB, and $S^1$ and $S^2$ represent a separator base sequence].

[6] The method for producing astrocyte-like cells according to any one of [3] to [5], in which the vector is a transposon vector.

[7] The method for producing astrocyte-like cells according to any one of [1] to [6], in which in the step (B), abundances of SOX9, NFIA, and NFIB in the human pluripotent stem cells satisfy 1:1:1 in terms of molar ratio.

[8] The method for producing astrocyte-like cells according to any one of [1] to [7], in which the human pluripotent stem cells are human induced pluripotent stem cells.

[9] Astrocyte-like cells that are produced by the production method according to any one of [1] to [8].

[10] A co-culture of the astrocyte-like cells according to [9] and nerve-like cells.

[11] Use of a culture medium containing a basic fibroblast growth factor or a culture medium containing at least one factor selected from the group consisting of brain-derived neurotrophic factor, glial cell line-derived neurotrophic factor, neurotrophin 3, and dibutyryl cyclic AMP, for the production of astrocyte-like cells.

It can also be said that the present invention includes the following aspects.

[P1] A method for producing astrocytes, including:

a step (A) of upregulating transcription factors including SRY-box transcription factor 9 (SOX9), nuclear factor IA (NFIA), and nuclear factor IB (NFIB) in human pluripotent stem cells; and a step (B) of culturing the human pluripotent stem cells, in which the transcription factors are upregulated, and consequently differentiating the human pluripotent stem cells into astrocytes.

[P2] The method for producing astrocytes according to [P1], in which in the step (B), the human pluripotent stem cells are cultured in a culture medium for pluripotent stem cell culturing or a culture medium for nerve cell culturing.

[P3] The method for producing astrocytes according to [P1] or [P2], in which the step (A) is carried out by introducing a vector containing a nucleic acid consisting of a base sequence encoding the transcription factor into the human pluripotent stem cells.

[P4] The method for producing astrocytes according to [P1] or [P2], in which the step (A) is carried out by adding or removing a tetracycline-based antibiotic to or from a culture medium of the human pluripotent stem cells into which vectors containing nucleic acids consisting of base sequences encoding the transcription factors under regulation of a tetracycline response element are introduced.

[P5] The method for producing astrocytes according to [P3] or [P4], in which the vector contains a nucleic acid consisting of a base sequence represented by Formula (P1), $$F^1—S^1—F^2—S^2—F^3 \quad (P1)$$

[in Formula (1), $F^1$, $F^2$, and $F^3$ represent, in no particular order, a base sequence encoding SOX9, a base sequence encoding NFIA, and a base sequence encoding NFIB, and $S^1$ and $S^2$ represent a separator base sequence].

[P6] The method for producing astrocytes according to any one of [P3] to [P5], in which the vector is a transposon vector.

[P7] The method for producing astrocytes according to any one of [P1] to [P6], in which in the step (B), abundances of SOX9, NFIA, and NFIB in the human pluripotent stem cells satisfy 1:1:1 in terms of molar ratio.

[P8] The method for producing astrocytes according to any one of [P1] to [P7], in which the human pluripotent stem cells are human induced pluripotent stem cells.

[P9] Astrocytes that are produced by the production method according to any one of [P1] to [P8].

[P10] A co-culture of the astrocytes according to [P9] and nerve cells.

[P11] Human pluripotent stem cells for producing astrocytes, into which nucleic acids consisting of base sequences encoding transcription factors including SOX9, NFIA, and NFIB are introduced.

[P12] The human pluripotent stem cells for producing astrocytes according to [P11], into which the nucleic acid consisting of the base sequences encoding the transcription factors under regulation of a tetracycline response element are introduced.

Advantageous Effects of Invention

According to the present invention, it is possible to efficiently produce astrocyte-like cells in vitro.

BRIEF DESCRIPTION OF THE DRAWINGS

FIG. 1 is a view showing an outline of Experimental Example 1.

FIG. 4A shows a graph of the result of quantitative RT-PCR in Experimental Example 4.

FIG. 4B shows a graph of the result of quantitative RT-PCR in Experimental Example 4.

DETAILED DESCRIPTION OF THE INVENTION

[Method for Producing Astrocyte-Like Cells]

Figure 2A:
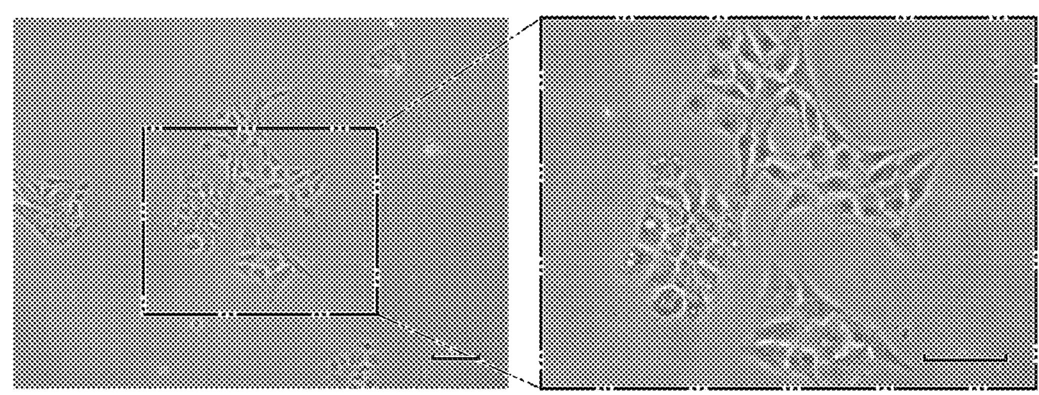
FIG. 2A shows photomicrographic images of the results of Experimental Example 2.

In one embodiment, the present invention provides a method for producing astrocyte-like cells, including a step (A) of upregulating transcription factors including SOX9, NFIA, and NFIB in human pluripotent stem cells, and a step (B) of culturing the human pluripotent stem cells, in which the transcription factors are upregulated, and consequently differentiating the human pluripotent stem cells into astrocyte-like cells.

In the present specification, an astrocyte-like cell means a cell that is functionally and morphologically equivalent to an astrocyte in vivo and thus can also be referred to as the astrocyte. The astrocyte-like cell expresses astrocyte markers described below.

As will be described later in Examples, according to the production method of the present embodiment, astrocyte-like cells can be efficiently produced in a short period of time. For example, 5 days after the initiation of transcription factor upregulation, cells that exhibit a morphology characteristic of astrocytes can be obtained under microscopic observation.

In addition, the efficiency of differentiation into astrocytes is high, meaning that the expression level of astrocyte markers is high as compared with a control. Examples of the astrocyte marker include glial fibrillary acidic protein (GFAP) and S100 calcium binding protein B (S100β).

The control includes cells in which any one of SOX9, NFIA, and NFIB is not upregulated. Specific examples thereof include cells in which only any one of SOX9, NFIA, and NFIB is upregulated, cells in which only SOX9 and NFIA are upregulated, cells in which only SOX9 and NFIB are upregulated, and cells in which only NFIA and NFIB are upregulated. As will be described later in Examples, the astrocytes obtained according to the method of the present embodiment, in which SOX9, NFIA, and NFIB are upregulated, have expression levels of astrocyte markers as high as about 4 to 7 times as compared with in a case where only SOX9 and NFIB are upregulated.

In the step (A), transcription factors including SOX9, NFIA, and NFIB are upregulated in human pluripotent stem cells. Here, upregulation means increasing the abundance in cells. Upregulating SOX9, NFIA, and NFIB may be, for example, introducing SOX9, NFIA, and NFIB into cells in the form of protein. Alternatively, SOX9, NFIA, and NFIB may be introduced into cells in the form of mRNA. Alternatively, expression vectors of the SOX9 gene, the NFIA gene, and the NFIB gene may be introduced into cells. Alternatively, SOX9, NFIA, and NFIB may be upregulated by preparing cells, into which expression vectors capable of regulating the expression of the SOX9 gene, the NFIA gene, and the NFIB gene have been introduced, and inducing the expression thereof.

The introduction of proteins, mRNAs, and expression vectors can be carried out by general methods as necessary, examples of which include electroporation, lipofection, and microinjection.

The expression vector may be a plasmid vector, may be a transposon vector, or may be a virus vector, or a combination thereof may be used.

The transposon vector may be such that it can be completely removed from cells as necessary. Examples of such a transposon vector include a PiggyBac vector.

Examples of the virus vector include a retrovirus vector, a lentivirus vector, an adeno-associated virus vector, and an adenovirus vector. In a case where the expression vector is a virus vector, it can be introduced into cells by infection.

Examples of the expression vector capable of regulating expression include those capable of regulating expression in response to external stimuli. Such expression vectors include at least a promoter capable of inducing the expression of a downstream gene in response to an external stimulus, and the SOX9 gene, the NFIA gene, and the NFIB gene, the expression of which is regulated by the promoter.

The promoter is not particularly limited as long as it can regulate the expression of the downstream gene in response to an external stimulus, and examples thereof include a promoter having a tetracycline response element (TRE) in a case where the external stimulus is the presence or absence of a tetracycline-based antibiotic.

In this case, the step (A) is carried out by adding or removing a tetracycline-based antibiotic to or from a culture medium of the human pluripotent stem cells into which vectors containing the SOX9 gene, the NFIA gene, and the NFIB gene under the regulation of the tetracycline response element are introduced.

In a case where the external stimulus is the presence of the tetracycline-based antibiotic (a Tet-On system), the expression of the downstream gene can be induced by binding a complex of a tetracycline-based antibiotic and a reverse tetracycline-controlled transactivator (rtTA) to TRE.

On the other hand, in a case where the external stimulus is the absence of a tetracycline-based antibiotic (a Tet-Off system), the expression of the downstream gene can be induced by binding a tetracycline-controlled transactivator (tTA) to TRE. In this case, in the presence of the tetracycline-based antibiotic, the tetracycline-based antibiotic forms a complex with tTA, which makes it impossible for tTA to bind to TRE, whereby the expression of the downstream gene is suppressed.

Examples of the tetracycline-based antibiotic include tetracycline derivatives such as tetracycline and doxycycline. In a case where doxycycline is used as the tetracycline-based antibiotic, the concentration of the doxycycline to be added to the culture medium can be 0.1 to 10 μg/mL, where 1 to 2 μg/mL is more preferable.

In addition, in a case where the external stimulus is the presence of an ecdysteroid, examples of the promoter include a promoter that can induce the expression of the downstream gene by the binding of the ecdysteroid to an ecdysone receptor-retinoid receptor complex. The ecdysteroid includes ecdysone, mirisetron A, ponasterone A, and the like.

In addition, in a case where the external stimulus is the presence of FKCsA, examples of the promoter include a promoter that can induce the expression of the downstream gene by the binding of FKCsA to a complex of a Gal4 DNA-binding domain fused to FKBP12 and a VP16 activator domain fused to cyclophilin The expression vector may contain an enhancer, a silencer, a drug selection marker, a replication origin, and the like, as necessary. Examples of the drug selection markers include a hygromycin resistance gene, a puromycin resistance gene, and a neomycin resistance gene.

The NCBI accession number of the SOX9 protein is N_000337.1 or the like. The NCBI accession number of the SOX9 cDNA is NM_000346.4 or the like. The NCBI accession number of the NFIA protein is NP_005586.1, NP_001128145.1, NP_001138984.1, or the like. The NCBI accession number of the NFIA cDNA is NM_001134673.4, NM_001145511.2, NM_001145512.2, or the like. The NCBI accession number of the NFIB protein is NP_001356409.1, NP_001356387.1, NP_001356397.1, or the like. The NCBI accession number of the NFIB cDNA is NM_001190737.2, NM_001190738.1, NM_001282787.1, or the like.

SOX9, NFIA, and NFIB may have a mutation as long as they have the activity of inducing the differentiation of human pluripotent stem cells into astrocyte-like cells. In a case where SOX9, NFIA, or NFIB has a mutation, it preferably has 80% or more sequence identity, more preferably has 90% or more sequence identity, and still more preferably has 95% or more sequence identity with the protein or cDNA identified by the NCBI accession number described above.

Here, the sequence identity of an amino acid sequence is a value indicating a ratio of matching between an amino acid sequence of interest (a target amino acid sequence) and an amino acid sequence as a reference (a reference amino acid sequence). The sequence identity of the target amino acid sequence with respect to the reference amino acid sequence can be determined, for example, as follows. First, a reference amino acid sequence and a target amino acid sequence are aligned. Here, each amino acid sequence may contain gaps to maximize sequence identity. Subsequently, the number of matching amino acids in the reference amino acid sequence and the target amino acid sequence is calculated, and the sequence identity can be determined according to Expression (F1).

$$\text{Sequence identity (\%)} = \text{number of matching amino acids} / \text{total number of amino acids in target amino acid sequence} \times 100 \quad \text{(F1)}$$

Similarly, the sequence identity of the target base sequence with respect to the reference base sequence can be determined, for example, as follows. First, a reference base sequence and a target base sequence are aligned. Here, each base sequence may contain gaps to maximize sequence identity. Subsequently, the number of matching bases in the reference base sequence and the target base sequence is calculated, and the sequence identity can be determined according to Formula (F2).

$$\text{Sequence identity (\%)} = \text{number of matching bases} / \text{total number of bases in target base sequence} \times 100 \quad \text{(F2)}$$

In the production method of the present embodiment, examples of the pluripotent stem cell include an embryonic stem cell (an ES cell) and an induced pluripotent stem cell (an iPS cell). In addition, the pluripotent stem cells may be cells derived from a healthy subject or may be cells derived from neurological disease patients. In a case where astrocyte-like cells are produced from pluripotent stem cells derived from neurological disease patients, the obtained astrocyte-like cells can be used as a model of the neurological disease. Such astrocyte-like cells are useful for elucidating the mechanism of the neurological disease.

Vectors that forcibly express the SOX9 gene, the NFIA gene, and the NFIB gene or vectors capable of inducing the expression of the SOX9 gene, the NFIA gene, and the NFIB gene may contain a nucleic acid consisting of a base sequence represented by Formula (1).

$$F^1—S^1—F^2—S^2—F^3 \quad (1)$$

In Formula (1), $F^1$, $F^2$, and $F^3$ represent, in no particular order, a base sequence encoding SOX9, a base sequence encoding NFIA, and a base sequence encoding NFIB, and $S^1$ and $S^2$ represent a separator base sequence.

$F^1$, $F^2$, and $F^3$ may be base sequences each encoding SOX9, NFIA, and NFIB, may be base sequences each encoding SOX9, NFIB, and NFIA, may be base sequences each encoding NFIA, NFIB, and SOX9, may be base sequences each encoding NFIA, SOX9, and NFIB, may be base sequences each encoding NFIB, SOX9, and NFIA, and may be base sequences each encoding NFIB, NFIA, and SOX9.

In addition, $S^1$ and $S^2$ may have the same base sequence or may have base sequences different from each other. In Formula (1), the separator base sequence is a base sequence that enables bicistronic expression, examples of which include an internal ribosome entry site (IRES) sequence and a 2A sequence. Examples of the 2A sequence include a T2A sequence derived from Thosea asigna, a P2A sequence derived from Porcine teschovirus, an F2A sequence derived from foot-and-mouth disease virus, and an E2A sequence derived from equine rhinitis A virus. The 2A sequence is also referred to as a self-cleaving peptide sequence.

Bicistronic expression means the expression of two or more proteins from a single mRNA. As a result, the expression levels of SOX9, NFIA, and NFIB become 1:1:1 in terms of molar ratio.

Note that the expression levels of SOX9, NFIA, and NFIB are capable of being adjusted to 1:1:1 in terms of molar ratio even without bicistronic expression, for example, by a method of introducing equimolar amounts of SOX9, NFIA, and NFIB into cells or a method of introducing equal copies of expression vectors that individually express SOX9, NFIA, and NFIB into cells.

Subsequently, in the step (B), human pluripotent stem cells in which SOX9, NFIA, and NFIB are upregulated are cultured. As a result, the human pluripotent stem cells differentiate into astrocyte-like cells. Since the astrocyte is a kind of glial cell, it is conceivable to use a culture medium for glial cell culturing as the culture medium in the step (B).

However, as will be described later in Examples, the inventors revealed that in a case where the step (B) is carried out using a culture medium for pluripotent stem cell culturing or a culture medium for nerve cell culturing, the expression level of astrocyte markers is increased as compared with a case of using a culture medium for glial cell culturing. That is, in a case of carrying out the step (B) using a culture medium for pluripotent stem cell culturing or a culture medium for nerve cell culturing, it is possible to efficiently produce astrocyte-like cells.

Examples of the culture medium for pluripotent stem cell culturing include a culture medium that is generally used for culturing iPS cells, ES cells, or the like. More specific examples thereof include Stem Fit (AK02N) (Ajinomoto Co., Inc.), Stem Fit (AK03) (Ajinomoto Co., Inc.), Cellartis DEF-CS 500 (Takara Bio Inc.), mTeRR1 (STEMCELL Technologies Inc.), mTeSR-E8 (STEMCELL Technologies Inc.), and Essential 8 (Thermo Fisher Scientific, Inc.). An additive may be added to the culture medium for pluripotent stem cell culturing. Examples of the additive include basic fibroblast growth factor (fibroblast growth factor 2, FGF2).

Examples of the culture medium for nerve cell culturing include a culture medium that is generally used for culturing of nerve cells. More specific examples thereof include KBM Neural Stem (Kohjin Bio Co., Ltd.), Neurobasal Medium (Thermo Fisher Scientific, Inc.), Neurobasal Plus Medium (Thermo Fisher Scientific, Inc.), and Brain Phys (STEMCELL Technologies Inc.). An additive may be added to the culture medium for nerve cell culturing. Examples of the additive include B27 Supplement (Thermo Fisher Scientific, Inc.), B27 Plus Supplement (Thermo Fisher Scientific, Inc.), N2 Supplement (Thermo Fisher Scientific, Inc.), SM1 Supplement (VERITAS Corporation), brain-derived neurotrophic factor (BDNF), glial cell line-derived neurotrophic factor (GDNF), neurotrophin 3 (NT3), and dibutyryl cyclic AMP (dbcAMP).

The production method of the present embodiment may have a step of differentiating human pluripotent stem cells into neural stem cells, or it may not have a step of differentiating human pluripotent stem cells into neural stem cells but be a method of directly inducing the differentiation of human pluripotent stem cells into astrocyte-like cells.

In a case where the production method of the present embodiment has a step of differentiating human pluripotent stem cells into neural stem cells, the human pluripotent stem cells may be first induced to differentiate into neural stem cells, and then, the step (A) of upregulating transcription factors including SOX9, NFIA, and NFIB in the cells induced to differentiate into neural stem cells and the step (B) of culturing the cells, in which the transcription factors are upregulated, and consequently differentiating the cells into astrocyte-like cells may be carried out.

As the step of differentiating human pluripotent stem cells into neural stem cells, a generally used method can be appropriately adopted. Examples thereof include a method of culturing human pluripotent stem cells in the presence of fibroblast growth factor 2 (FGF2), a Rho-associated protein kinase (ROCK) signal transduction pathway inhibitor, and a leukemia inhibitory factor (LIF).

Examples of the ROCK signal transduction pathway inhibitor include Y-27632 (CAS number: 129830-38-2), Fasudil/HA1077 (CAS number: 105628-07-7), H-1152

(CAS number: 871543-07-6), Wf-536 (CAS number: 539857-64-2), and derivatives thereof.

The final concentration of the ROCK signal transduction pathway inhibitor in the culture medium is generally 0.1 μM to 100 μM, preferably 5 μM to 50 μM, and more preferably 10 μM to 30 μM.

[Astrocyte-Like Cells]

In one embodiment, the present invention provides astrocyte-like cells produced by the production method described above. Since the astrocyte-like cells of the present embodiment can be efficiently produced in vitro, they can be suitably used for basic research, elucidation of nervous system diseases, and the like.

The exogenous SOX9 gene, NFIA gene, and NFIB gene may be introduced into the genome of the astrocyte-like cell of the present embodiment. In addition, the SOX9 gene, NFIA gene, and NFIB gene may be linked through a separator base sequence.

[Co-Culture]

In one embodiment, the present invention provides a co-culture of the above-described astrocyte-like cells and nerve-like cells.

In the present specification, the nerve-like cell means a cell that is functionally and morphologically equivalent to a nerve cell in vivo and thus can also be referred to as a nerve cell. The nerve-like cell expresses nerve cell markers such as microtubule-associated protein 2 (MAP2), synapsin 1 (SYN1), and βIII-tubulin (TUBB3).

As described above, the brain organoids produced from pluripotent stem cells are mainly composed of nerve cells and neural stein cells but do not contain fully mature glial cells. On the other hand, according to the co-culture of the present embodiment, a large amount of prepared astrocyte-like cells and nerve-like cells can be co-cultured, which makes it possible to analyze the functions of nerve cells in a state close to in vivo.

[Use of Culture Medium for Production of Astrocyte-Like Cells]

In one embodiment, the present invention provides use of a culture medium containing a basic fibroblast growth factor or a culture medium containing at least one factor selected from the group consisting of brain-derived neurotrophic factor, glial cell line-derived neurotrophic factor, neurotrophin 3, and dibutyryl cyclic AMP, for the production of astrocyte-like cells. As described above, the use of the present embodiment enables the efficient production of astrocyte-like cells in vitro.

EXAMPLES

Next, the present invention will be described in more detail by showing experimental examples; however, the present invention is not limited to the experimental examples below.

Experimental Example 1

(Differentiation of iPS Cells into Astrocyte-Like Cells)

SOX9, NFIA, and NFIB were expressed in human iPS cells, and the differentiation into astrocyte-like cells was examined. FIG. 1 is a view showing an outline of the experiment. First, using a transposon vector (a PiggyBac vector, VectorBuilder Inc.), a reverse tetracycline-controlled transactivator (rtTA3G, VectorBuilder Inc.) was introduced into human iPS cells (a 1210B2 line), and the gene-introduced line was selected by drug selection. The hygromycin resistance gene was used as a drug selection marker for rtTA3G. An internal ribosome entry site (IRES) sequence was introduced between the rtTA3G and hygromycin resistance genes to bicistronically express these genes. HyPBase (VectorBuilder Inc.) was used as the transposase.

Subsequently, using a lentivirus vector (VectorBuilder Inc.), the SOX9 gene, the NFIB gene, and the NFIA gene under the regulation of the tetracycline response element were introduced into a cell line stably expressing rtTA3G, and the gene-introduced line was selected by drug selection. The puromycin resistance gene was used as a drug selection marker. The T2A sequence was introduced between the SOX9 gene, the NFIB gene, and the NFIA gene to bicistronically express these genes. In addition, a base sequence encoding a FLAG tag was added to the SOX9 gene.

In addition, using a lentivirus vector (VectorBuilder Inc.), the SOX9 gene and the NFIB gene under the regulation of the tetracycline response element were introduced for comparison into a cell line stably expressing rtTA3G, and the gene-introduced line was selected by drug selection. The puromycin resistance gene was used as a drug selection marker. The T2A sequence was introduced between the SOX9 gene and the NFIB gene to bicistronically express these genes. In addition, a base sequence encoding a FLAG tag was added to the SOX9 gene.

Subsequently, the obtained gene-introduced line was subjected to expansion culturing for 6 days. As the culture medium, a culture medium for pluripotent stem cell culturing (product name "Stem Fit (AK02N)", Ajinomoto Co., Inc.) was used.

Cells were then dissociated and seeded in a new plate coated with Matrigel to induce differentiation into astrocyte-like cells. In addition, doxycycline was added to the culture medium to induce the expression of the SOX9 gene, NFIB gene, and NFIA gene, or the SOX9 gene and the NFIB gene. As the culture medium, a culture medium for pluripotent stem cell culturing, a culture medium for glial cell culturing, and a culture medium for nerve cell culturing were used and compared.

As the culture medium for pluripotent stem cell culturing, a culture medium obtained by adding "Stem Fit (AK02N) B solution" (product name) (Ajinomoto Co., Inc.) and "Stem Fit (AK02N) C solution (product name) (Ajinomoto Co., Inc.) to a basal medium (product name "Stem Fit (AK02N) A solution", Ajinomoto Co., Inc.) was used.

As the culture medium for glial cell culturing, a culture medium obtained by adding 2% B27 Supplement (Thermo Fisher Scientific, Inc.), 1% Glutamax (Thermo Fisher Scientific, Inc.), 1% non-essential amino acids (NEAA) (FUJIFILM Wako Pure Chemical Corporation), 20 ng/mL fibroblast growth factor (FGF), 10 ng/mL epidermal growth factor (EGF), and 10 ng/mL neurotrophin 3 (NT3) to a basal medium (product name "KBM Neural Stem", Kohjin Bio Co., Ltd.) was used.

As the culture medium for nerve cell culturing, a culture medium obtained by adding 2% B27 Supplement (Thermo Fisher Scientific, Inc.), 1% Glutamax (Thermo Fisher Scientific, Inc.), 1% CultureOne Supplement (Thermo Fisher Scientific, Inc.), 200 μM ascorbic acid, 20 ng/mL brain-derived neurotrophic factor (BDNF), 20 ng/mL glial cell line-derived neurotrophic factor (GDNF), 20 ng/mL neurotrophin 3 (NT3), and 100 μM dibutyryl cyclic AMP (db-cAMP) to a basal medium (product name "Neurobasal Plus Medium", Thermo Fisher Scientific, Inc.) was used.

Experimental Example 2

(Microscopic Observation of Astrocyte-Like Cells)

Figure 2B:
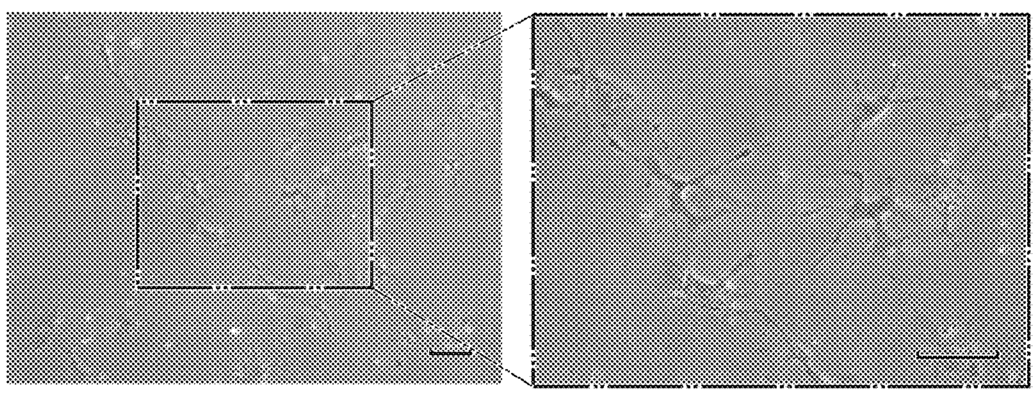
FIG. 2B shows photomicrographic images of the results of Experimental Example 2.

Cells induced to differentiate into astrocyte-like cells in Experimental Example 1 were observed under a microscope. FIG. 2A and FIG. 2B show photographic images of the results of microscopic observation of the cells cultured for 5 days in the presence or absence of doxycycline in Experimental Example 1. These are representative results using the culture medium for nerve cell culturing as the culture medium. The scale bar is 100 μm.

FIG. 2A shows photographic images of cells cultured in the absence of doxycycline, and FIG. 2B shows photographic images of cells cultured in the presence of doxycycline. In FIG. 2A and FIG. 2B, the photographic image on the right is an enlarged photographic image of the area enclosed by the square in the photographic image on the left.

As a result of the above observation, it was revealed that in the presence of doxycycline, the cells in which the expressions of the SOX9 gene, the NFIB gene, and the NFIA gene are induced exhibit a morphology characteristic of astrocytes even though only 5 days after the initiation of the expression induction.

Experimental Example 3

(Examination by Immunochemical Staining)

The cells induced to differentiate into astrocyte-like cells in Experimental Example 1 were fixed and subjected to immunochemical staining. FIG. 3A to FIG. 3E show fluorescence photomicrographic images of the results obtained by subjecting the cells cultured for 20 days in the presence of doxycycline to paraformaldehyde fixing and immunochemical staining. These are representative results using the culture medium for nerve cell culturing as the culture medium. The scale bar is 100 μm.

Figures 3A, 3B, 3C, 3D, 3E:
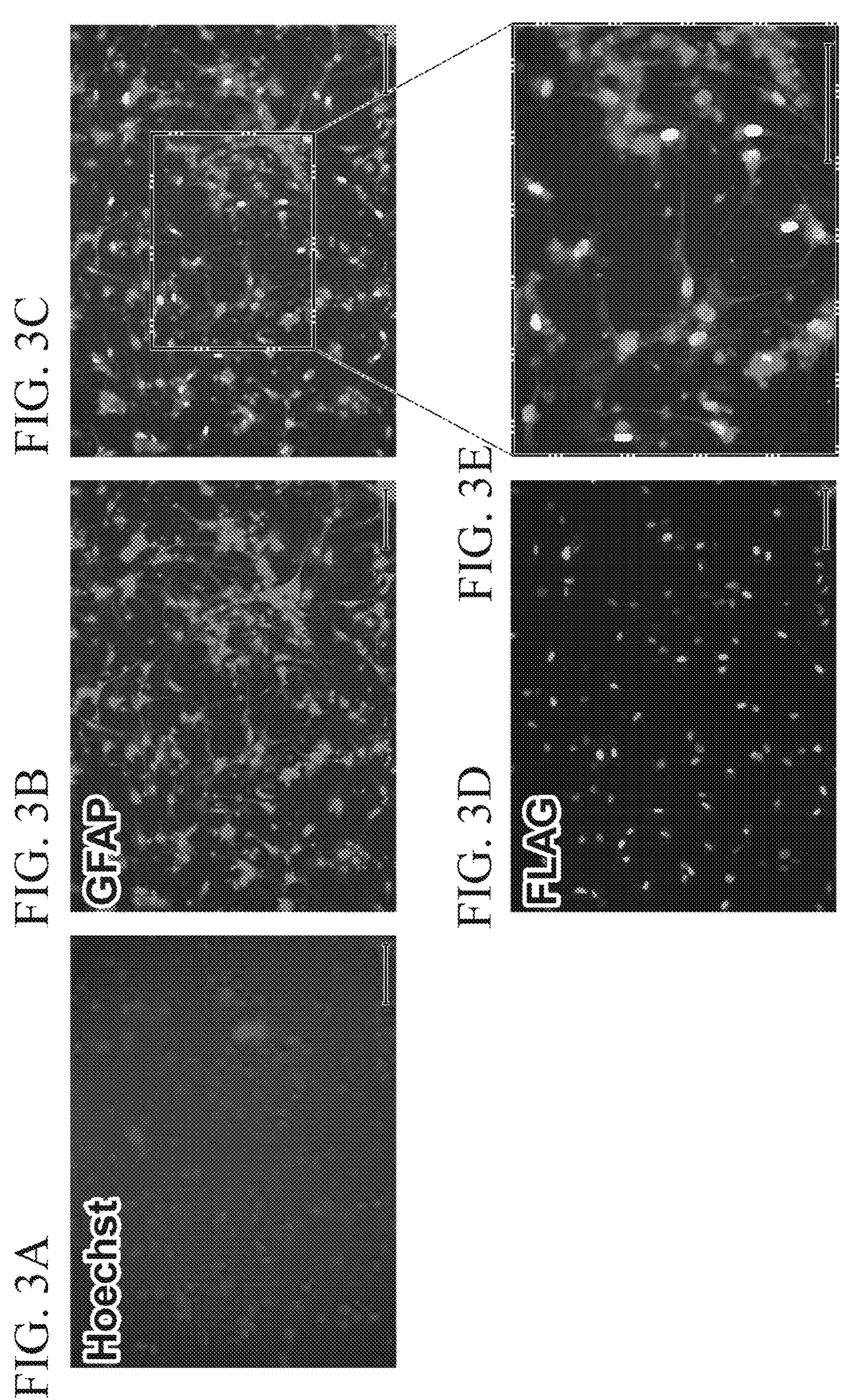
FIG. 3A shows a fluorescence photomicrographic image of the result of Experimental Example 3.
FIG. 3B shows a fluorescence photomicrographic image of the result of Experimental Example 3.
FIG. 3C shows a fluorescence photomicrographic image of the result of Experimental Example 3.
FIG. 3D shows a fluorescence photomicrographic image of the result of Experimental Example 3.
FIG. 3E shows a fluorescence photomicrographic image of the result of Experimental Example 3.

FIG. 3A shows the results of staining the nucleus with Hoechst 33342. FIG. 3B shows the results of staining GFAP, an astrocyte marker, with an anti-GFAP antibody. FIG. 3C shows the results of staining the FLAG tag with an anti-FLAG antibody. As described above, since the SOX9 gene was added with a base sequence encoding the FLAG tag, the expression of SOX9 can be detected with an anti-FLAG antibody. FIG. 3D shows the photographic image obtained by combining FIG. 3B and FIG. 3C. FIG. 3E shows an enlarged photographic image of the area enclosed by the square of FIG. 3D. As a result of the examination, the expression of GFAP was confirmed, and it was revealed that the cells had differentiated into astrocytes.

Experimental Example 4

(Examination by Quantitative RT-PCR)

The mRNAs of astrocyte markers in each cell cultured for 20 days in the presence of doxycycline in Experimental Example 1 were quantified by quantitative RT-PCR. GFAP and S100β were examined as astrocyte markers. Cells cultured using a culture medium for nerve cell culturing as the culture medium were used.

Figures 4A, 4B:
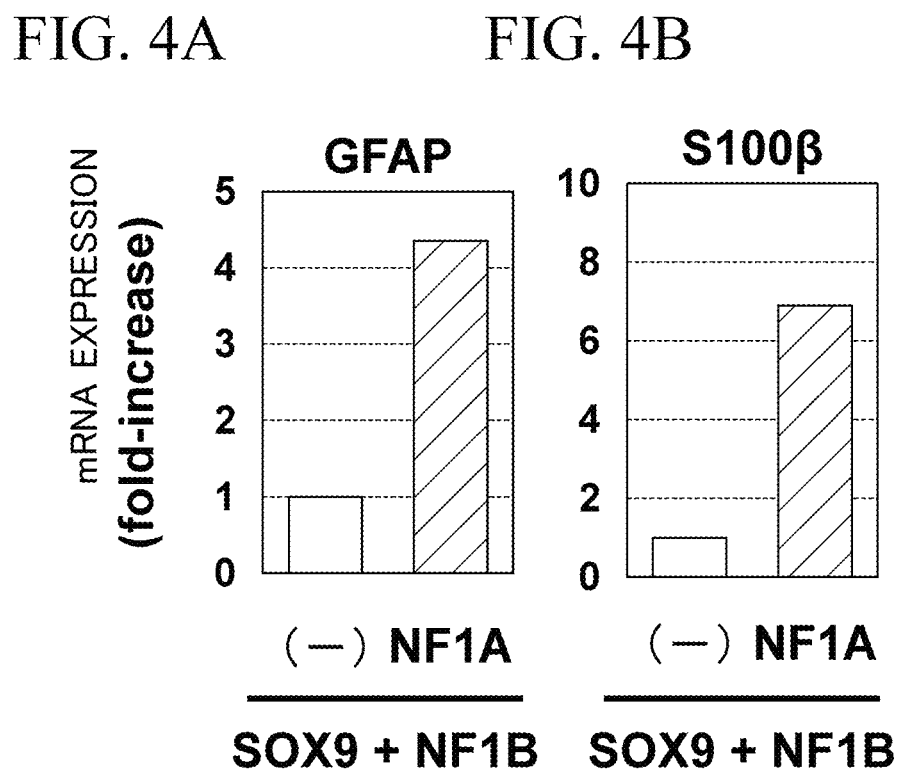

FIG. 4A and FIG. 4B show graphs of the results of quantitative RT-PCR. FIG. 4A shows the results of GFAP, and FIG. 4B shows the results of S100β. In FIG. 4A and FIG. 4B, "(−)" indicates the results of cells in which the expression of the SOX9 gene and the NFIB gene was induced, and "NFIA" indicates the results of cells in which the expression of the SOX9 gene, the NFIA gene, and the NFIB gene was induced. The vertical axis indicates the expression level of mRNA, where the expression level is shown as a relative value in a case where the result of the cells in which the expression of the SOX9 gene and the NFIB gene was induced is set to 1.

As a result of the examination, it was revealed that in the cells in which the expression of the SOX9 gene, the NFIA gene, and the NFIB gene had been induced, the expression level of GFAP is 4 times or more and the expression level of S100β is approximately 7 times as compared with cells in which the expression of the SOX9 gene and the NFIB gene had been induced.

Experimental Example 5

(Examination of Culture Medium)

The mRNAs of astrocyte markers in each cell, in which the expression of the SOX9 gene, the NFIA gene, and the NFIB gene had been induced, cultured for 20 days in the presence of doxycycline in Experimental Example 1 were quantified by quantitative RT-PCR. GFAP and S100β were examined as astrocyte markers. As the culture medium, a culture medium for pluripotent stem cell culturing, a culture medium for glial cell culturing, and a culture medium for nerve cell culturing were used.

Figures 5A, 5B:
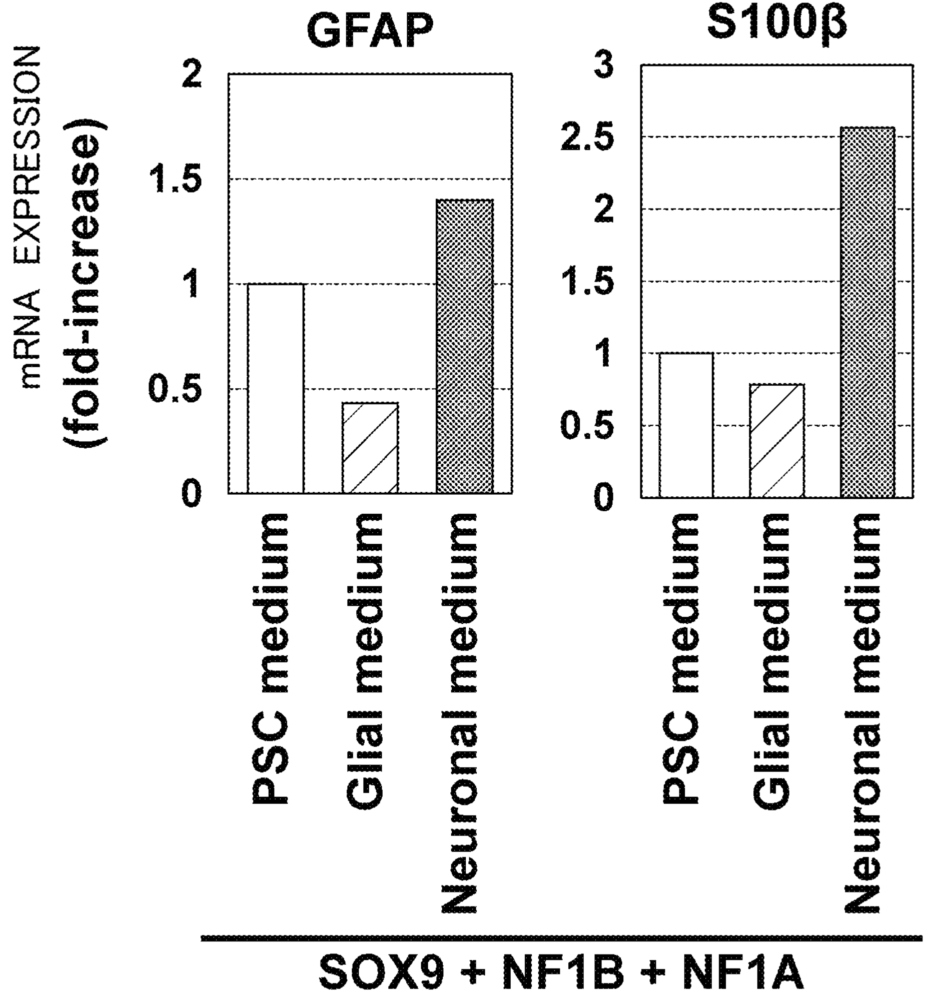
FIG. 5A shows a graph of the result of quantitative RT-PCR in Experimental Example 5.
FIG. 5B shows a graph of the result of quantitative RT-PCR in Experimental Example 5.

FIG. 5A and FIG. 5B show graphs of the results of quantitative RT-PCR. FIG. 5A shows the results of GFAP, and FIG. 5B shows the results of S100β. In FIG. 5A and FIG. 5B, "PSC medium" is the result obtained by using the culture medium for pluripotent stem cell culturing, "Glial medium" is the result obtained by using the culture medium for glial cell culturing, and "Neuronal medium" is the result obtained by using the culture medium for nerve cell culturing. The vertical axis indicates the expression level of mRNA, where the expression level is shown as a relative value in a case where the result obtained by using the culture medium for pluripotent stem cell culturing is set to 1.

As a result of the above examinations, it was revealed that the expression level of astrocyte markers is high in a case where culturing is carried out in the culture medium for pluripotent stem cell culturing or the culture medium for nerve cell culturing as compared with the culture medium for glial cell culturing, which is conceived to be originally suitable for astrocyte culturing.

INDUSTRIAL APPLICABILITY

According to the present invention, it is possible to efficiently produce astrocyte-like cells in vitro.

What is claimed is:

1. A method for producing astrocyte-like cells, comprising:

(A) upregulating transcription factors including SRY-box transcription factor 9 (SOX9), nuclear factor IA (NFIA), and nuclear factor IB (NFIB) in human pluripotent stem cells; and (B) culturing the human pluripotent stem cells, in which the transcription factors are upregulated, and consequently differentiating the human pluripotent stem cells into astrocyte-like cells, wherein (A) upregulating is carried out by introducing a vector containing nucleic acids encoding the transcription factors into the human pluripotent stem cells, wherein the vector contains a nucleic acid consisting of a base sequence represented by Formula (1), $$F^1—S^1—F^2—S^2—F^3 \quad (1),$$

wherein in Formula (1), $F^1$, $F^2$, and $F^3$ represent, in no particular order, a base sequence encoding SOX9, a base sequence encoding NFIA, and a base sequence encoding NFIB, and $S^1$ and $S^2$ represent a separator base sequence, whereby in (B) culturing, abundances of SOX9, NFIA, and NFIB in the human pluripotent stem cells satisfy 1:1:1 in terms of molar ratio.

2. The method for producing astrocyte-like cells according to claim 1, wherein in (B) culturing, the human pluripotent stem cells are cultured in a culture medium for pluripotent stem cell culturing or a culture medium for nerve cell culturing.

3. The method for producing astrocyte-like cells according to claim 2, wherein the culture medium for pluripotent stem cell culturing comprises a basic fibroblast growth factor and the culture medium for nerve cell culturing comprises at least one factor selected from the group consisting of brain-derived neurotrophic factor, glial cell line-derived neurotrophic factor, neurotrophin 3, and dibutyryl cyclic AMP.

4. The method for producing astrocyte-like cells according to claim 1, wherein (A) upregulating is carried out by adding or removing a tetracycline-based antibiotic to or from a culture medium of the human pluripotent stem cells and the vector contains the nucleic acids encoding the transcription factors under regulation of a tetracycline response element.

5. The method for producing astrocyte-like cells according to claim 1, wherein the vector is a transposon vector.

6. The method for producing astrocyte-like cells according to claim 1, wherein the human pluripotent stem cells are human induced pluripotent stem cells.

7. Astrocyte-like cells that are produced by the production method according to claim 1.

8. A co-culture of the astrocyte-like cells according to claim 7 and nerve-like cells.

* * * * *